United States Patent [19]

Seth

[11] Patent Number: 5,571,097
[45] Date of Patent: Nov. 5, 1996

[54] ADHESIVE TAPE TAB CLOSURE SYSTEM

[75] Inventor: Jayshree Seth, Woodbury, Minn.

[73] Assignee: Minnesota Mining and Manufacturing Company, St. Paul, Minn.

[21] Appl. No.: 346,486

[22] Filed: Nov. 29, 1994

[51] Int. Cl.⁶ .................................................. A61F 13/15
[52] U.S. Cl. ............................ 604/389; 604/390
[58] Field of Search ........................ 604/389, 390, 604/385.1, 358

[56]  References Cited

U.S. PATENT DOCUMENTS

| | | | |
|---|---|---|---|
| 3,952,744 | 4/1976 | Aldinger | 604/390 |
| 3,955,576 | 5/1976 | Safford | 128/287 |
| 4,029,098 | 6/1977 | Karami | 128/284 |
| 4,060,085 | 11/1977 | Karami | 128/287 |
| 4,168,196 | 9/1979 | Nemeth et al. | 156/184 |
| 4,237,890 | 12/1980 | Laplanche | 128/287 |
| 4,345,597 | 8/1982 | Tritsch | 604/390 |
| 4,643,729 | 2/1987 | Laplanche | 604/390 |
| 4,726,971 | 2/1988 | Pape et al. | 428/40 |
| 4,769,283 | 9/1988 | Sipinen et al. | 428/343 |
| 5,049,145 | 9/1991 | Flug | 604/391 |
| 5,053,028 | 10/1991 | Zoia et al. | 604/389 |
| 5,212,011 | 5/1993 | Ishikawa et al. | 428/343 |
| 5,288,546 | 2/1994 | Roessler et al. | 604/389 |
| 5,342,685 | 8/1994 | Gobran | 428/355 |

FOREIGN PATENT DOCUMENTS

| | | | |
|---|---|---|---|
| 0191355 | 8/1986 | European Pat. Off. | A41B 13/02 |
| 87/05471 | 9/1987 | WIPO | A41B 13/02 |
| 92/04001 | 3/1992 | WIPO | A61F 13/62 |

OTHER PUBLICATIONS

PCT International Application No. WO94/10837

Primary Examiner—John G. Weiss
Assistant Examiner—David J. Cho
Attorney, Agent, or Firm—Gary L. Griswold; Walter N. Kirn; William J. Bond

[57]  ABSTRACT

A disposable tape tab closure system for a diaper or a like article is provided with at least a fastening tape tab portion and a release tape tab portion, the fastening tape tab portion having an adhesive surface opposite the release surface face of a release tab portion the two tabs forming a laminate attached to one face of a disposable garment. The fastening tape tab portion attached to a second face of the disposable garment by a pressure-sensitive adhesive hinge tape with no adhesive bond between the fastening tape tab and the release tape tab.

10 Claims, 3 Drawing Sheets

ADHESIVE TAPE TAB CLOSURE SYSTEM

The present invention relates to an adhesive closure fastening tape tab and release tape tab structure for use in a disposable diaper or an adult incontinent article.

Most disposable diapers use pressure-sensitive adhesive fastening tape tabs. The adhesive on the free end, or outer end of the fastening tape tab requires protection from contamination prior to use. This protection was originally provided with a disposable release liner. However, early disposable release liners were considered to be undesirable for a number of reasons, including; inconvenience, difficulty of use and fear that a baby might inadvertently swallow the detachable disposable release liner. In response to these problems a number of patent applications were filed directed at various means of eliminating or modifying the disposable release liner. Some of these patents are discussed in U.S. Pat. No. 4,168,196.

U.S. Pat. No. 4,168,196 is directed to a method of eliminating the disposable release liner while minimizing the amount of substrate film used in forming the diaper fastening tape tab. A single substrate film is zone coated with adhesive and release material, respectively, on opposing faces and ends of the substrate film. There are two adhesive regions on different faces, and opposing ends, of the substrate with two release coated regions provided opposite the two adhesive regions so that the substrate can be wound as a tape with the two adhesive regions in contact with the two release coatings. The fastening tape tab is adhered to the non-woven topsheet of the diaper with one adhesive region. The second adhesive region on the opposing end and face of the fastening tape tab is attached to the diaper backsheet by the user. This system, while relatively simple to use by the diaper manufacturer, is extremely difficult to manufacture, requiring complicated zone coating of two distinct release coatings and two adhesive layers in close proximity on both faces of a single substrate backing.

A more typical approach was the use of a separate fastening tape tab and a separate release tape tab or release liner where the release tape tab or release liner is permanently secured to the diaper, the fastening tape tab or both. For example, U.S. Pat. No. 3,955,576 proposes attaching a fastening tape tab to a release tape tab, which release tape tab is also permanently attached to the diaper topsheet. The permanent attachment between the fastening tape tab and the release tape tab is created by overlapping and folding the tapes to form an adhesive-to-adhesive contact region between the two tape tabs. U.S. Pat. No. 4,237,890 provides a release liner which is permanently attached at one face to a central section or zone of a fastening tape tab. One end section of the fastening tape tab is releasably attached to the release liner and the opposing end section of the fastening tape tab is permanently attached to the diaper backsheet. The two attached tabs would apparently be supplied as a folded prelaminate structure. Another folded prelaminate structure is disclosed in U.S. Pat. No. 4,726,971 where a release tape tab is secured to a fastening tape tab by a unifying strip. Further, the fastening tape tab and the release tape tab are permanently attached to opposing faces of the diaper. The fastening tape tab fastening end section is releasably secured to the release surface of the release tape tab. The fastening tape tab end permanently adhered to the diaper is provided with a distinct more aggressive adhesive layer. U.S. Pat. Nos. 4,060,085 and 4,029,098 propose a release liner which is adhesively secured to a central portion of the fastening tape tab at one end section with most of the release liner heat sealed to the inner topsheet face of the diaper. These constructions are much more difficult for a diaper manufacturer to implement and heat sealing of the release liner to the diaper may effectively destroy the release characteristics of the release surface.

The present invention is directed at providing a low cost pressure-sensitive adhesive fastening tape tab and release tab laminate which is both simple to apply and use by the diaper manufacturer and simple to manufacture forming a low cost, high performance diaper tape tab closure system.

SUMMARY OF THE INVENTION

According to the present invention, a disposable garment, e.g. a diaper or adult incontinent article, is provided with a pressure-sensitive adhesive closure tape tab system comprising a closure tab laminate, of a fastening tape tab portion and a release tab portion, and a hinge tape. The fastening tape tab portion has a first face with an adhesive layer and a second opposing face with no adhesive layer. The release tab portion has a first face with a release layer and a second face with no release layer. The release tab and fastening tape tab are laminated and wound into a roll of closure laminate and subsequently unwound and cut into closure tab laminates for application to a disposable garment. The fastening tape tab first face and the release tab first face are laminated in overlying arrangement such that at least the fastening tape tab adhesive layer is covered by the release layer of the release tab, allowing the fastening tape tab portion first face to be removed from the release tab portion first face.

The release tab portion is permanently adhered to the disposable garment by the release tab second face. The fastening tape tab portion is releasably attached to the release tab portion first face and permanently attached to the disposable garment with the hinge tape. The hinge tape first face is adhered at one end to the second face of the fastening tape tab portion. The hinge tape second end is adhered to an outer face of the disposable garment. The release tab portion is attached to an inner face of the disposable garment by an adhesive layer on the release tab portion second face.

When the closure laminate is formed, with the two tabs flat and in the same plane, the two tab first faces are in face-to-face relation and substantially fully overlapping. The two tabs are removable from each other such that there is no adhesive contact between the fastening tape tab adhesive layer and a non-release coated surface of the release tab portion first or second faces.

If the closure laminate is to be directly cut into closure tab laminates and applied by a disposable garment manufacturer as a tape, the release tab second face is coated with a pressure-sensitive adhesive and the fastening tape tab second face is preferably coated with a release coating such that a closure tape laminate can be wound into a roll, unwound, then cut into closure tape tab laminates and applied to the disposable garment as a pressure-sensitive adhesive closure tape tab laminate. Alternatively, the disposable garment manufacturer can adhesive coat the closure laminate release tab second face after a nontape closure laminate is unwound and before applying the closure tab laminate on the disposable garment. The hinge tape can also be supplied as a roll of pressure-sensitive adhesive tape or formed from a film that is adhesive coated prior to being cut into tabs.

When in use as a diaper tape tab closure system, the closure tab laminate release tab portion second face is adhered to a diaper topsheet (the liquid permeable inner layer) at a first edge region of the diaper. The fastening tape tab portion adhesive layer is releasably secured to a release surface on the first face of the release tab portion such that the fastening tape tab portion may be removed from the release tab portion and subsequently adhered to the diaper backsheet at a second edge region of the diaper to form the diaper closure. The hinge tape secures the fastening tape tab portion to the diaper backsheet at the first edge region of the diaper.

DETAILED DESCRIPTION OF THE PREFERRED EMBODIMENTS

The pressure-sensitive adhesive closure tape tab system of the present invention will generally be described with reference to disposable diapers and adult incontinent articles, however, the invention closure tape tab system would be applicable to other disposable garments, for example, a hospital gown, disposable cap or in packaging, such as for an individual sanitary napkin wrapper.

Figure 1:
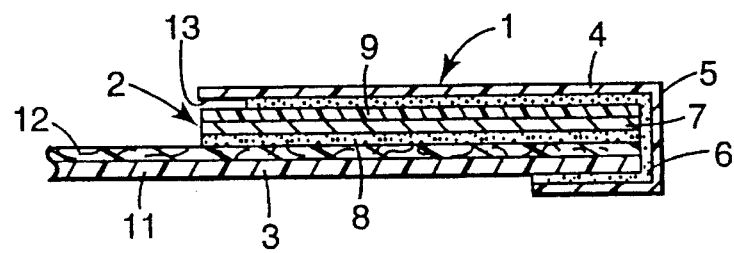
FIG. 1 is a side cross-sectional view of a prior art closure tape tab system on a diaper side edge.

FIG. 1 shows a conventional method of attaching a fastening tape tab 1 to a diaper outer edge region 3. The outer edge region 3 would comprise a web or laminate of a film and/or a nonwoven. The fastening tape tab 1 would comprise a backing 5 with a release surface and a pressure-sensitive adhesive layer 6. One end of the fastening tape tab 1 would be releasably attached to a release tape tab 2 and a second opposing end of the fastening tape tab 1 is attached to the outer edge region 3 of the diaper. The two tape tabs 2 and 1 are applied from separate rolls of tapes. Problems with this construction include cost and performance. The adhesive layer 6 must be designed to securely and permanently bond to edge region 3 at the second end while releasably bonding to a front portion of the diaper at the first end of the pressure-sensitive adhesive fastening tape tab 1. These inherently inconsistent objectives can cause problems with the adhesive attachment objectives at either, or both, ends of the fastening tape tab 1. Manufacturability can also be difficult due to exposed adhesive on the fastening tape tab during manufacture and the need to precisely fold the fastening tape tab, at the junction between the first and second ends, into the adhesive coated face.

Figure 2:
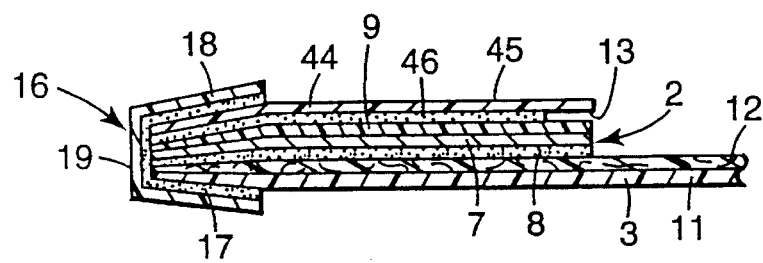
FIG. 2 is a side cross-sectional view of a first embodiment of the invention closure tape tab system on a diaper side edge.
Figure 3:
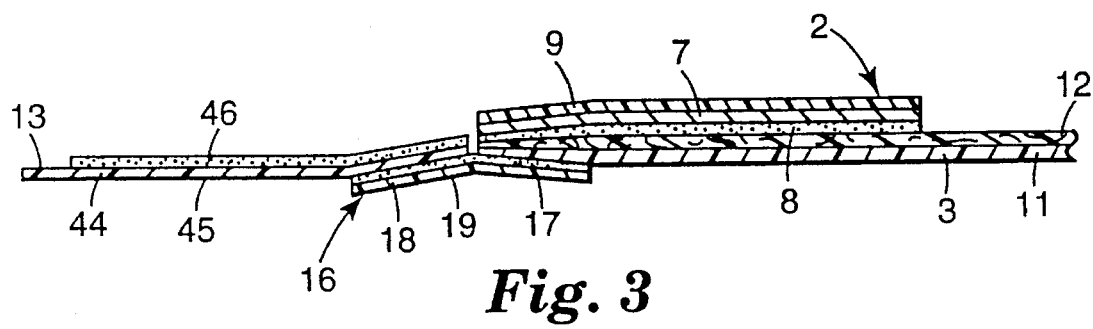
FIG. 3 is a side cross-sectional view of a first embodiment of the invention closure tape tab system as it would be used.

FIG. 2 discloses a first embodiment of the present invention where the closure tape tab system comprises a release tab portion 2, a fastening tape tab portion 41 and a hinge tape 16. The closure tape tab system is permanently attached to an edge region 3 of the diaper 10 comprising a liquid permeable topsheet layer 12 and a liquid impermeable backsheet layer 11, which two layers, or only one of these two layers, comprise the diaper 10 edge region 3. This outer edge region 3 is where the closure tape tab system is attached. The two tab portions (41 and 2) are laminated to each other such that an adhesive layer on the fastening tape tab portion 41 is releasably adhered to a release layer 9 on the release tab portion 2.

The release tab portion 2 comprises a substrate 7 provided with a release surface 9 on a first face with a second face permanently attached to the outer edge region 3, preferably with a pressure-sensitive adhesive layer 8. Substrate 7 can be any conventional film, such as a single or multi-layer film of a thermoplastic polymer or polymers, such as polyolefins. Also, a nonwoven or woven substrate can be extrusion coated or laminated to additional layers, paper, films or the like to form substrate 7. The release surface 9 would typically be a release coating, which would be any type conventionally used as a release coating on a diaper release tape or release liner.

Pressure-sensitive adhesive layer 8, if used, is formulated with an adhesive which will permanently bond the release tab portion 2 to the outer edge region 3 and would conventionally be a resin tackified rubber or synthetic rubber-type adhesive. A preferred adhesive would comprise that disclosed in U.S. Pat. No. 5,342,685 (Gobran), which discloses an adhesive comprising 100 parts of an elastomeric phase having 78–98 parts of an elastomeric diblock A-B type block copolymer of predominantly polystyrene, or polystyrene derivative, A blocks, and poly-1,3-butadiene B blocks. The remaining portion of the elastomeric phase comprises multi-block A-B type block copolymers of three or more blocks, preferably an ABA triblock copolymer with the B block a poly-1,3-butadiene. The elastomeric phase is tackified with an admixture of a solid tackifying resin and an oil or liquid tackifier, at lease partially compatible with the B blocks, to provide an adhesive having a composite midblock glass transition temperature (CMTg) of less than −10° C. Other tackified synthetic rubber or natural rubber pressure-sensitive adhesives can be used provided that the initial 135° peel (tested as described in U.S. Pat. No. 5,342,685) to the diaper topsheet, e.g. a nonwoven, is at least 100 gm/25.4 mm, preferably at least 150 gm/25.4

Fastening tape tab portion 41 similarly is comprised of a substrate 44 which can be any suitable substrate, such as those described for the release tape tab portion substrate 7, conventionally used as a tape backing. The fastening tape tab adhesive layer 46 can be any conventional pressure-sensitive adhesive used for a repositionable diaper fastening tape tab. In a preferred embodiment, a less aggressive adhesive is used as the fastening tape tab adhesive 46.

The fastening tape tab adhesive is preferably a tackified elastomer adhesive where the elastomer is preferably a thermoplastic AB type block copolymers having A blocks and B blocks, such as A-B-A block copolymers and A-B block copolymers. The A block is a monoalkenyl arene, mainly polystyrene, having a molecular weight between 4,000 and 50,000, preferably between 7,000 and 30,000. The A block content is from about 10 to 50 percent, more preferably between 10 and 30 percent. Other suitable A blocks may be formed from alphamethyl styrene, t-butyl styrene and other ring alkylated styrenes as well as mixtures thereof. B is an elastomeric conjugated diene, such as isoprene or butadiene or hydrogenated versions thereof, having an average molecular weight of from about 5,000 to about 500,000, preferably from about 50,000 to 200,000. Although preferably AB type block copolymers will comprise the majority of the elastomer of the adhesive, other conventional diene elastomers may be used to a minor extent, such as natural rubber; butadiene, isoprene or butadiene-styrene rubber; butadiene-acrylonitrile; butyl rubber or block copolymers of these diene elastomers. The block copolymer is used in an amount ranging from about 30 to 95 weight percent, preferably 35 to 60 weight percent of the adhesive composition.

The tackifying resin component generally comprises a blend of a solid tackifying resin and a liquid tackifying resin, solid tackifying resin, liquid tackifying resin, or a blend of a solid tackifying resin and a liquid plasticizer and/or a liquid tackifying resin. The tackifying resins can be selected from the group of resins at least partially compatible with the B blocks of the elastomeric materials. The adhesive preferably is tackified with a solid tackifying resin with a liquid plasticizer or liquid resin. The adhesive can be applied by any conventional method including hot melt coating, gravure coating, coextrusion, solvent coating and the like.

The fastening tape tab adhesive can generally have a CMTg of from 230 to 265 Kelvin. The polymer content is generally higher for lower CMTg adhesive formulations and lower for higher CMTg formulations. The CMTg can be calculated using the Fox Equation by measuring the Tg of the midblock of the elastomeric block copolymer and the Tg of each tackifying resin and liquid plasticizer oil. The Tg for each component is measured using a differential scanning calorimeter such as a DSC-7, manufactured by Perkin-Elmer.

Less aggressive adhesives are useful for when the fastening tape tab portion 41 is adhered directly to a thin film, or the like, backsheet layer to form the adhesive closure. This, e.g., thin film is generally a polyethylene polymer, copolymer or blend film.

Optionally, a pressure-sensitive adhesive free region 13 can be provided at the outer end of the fastening tape tab portion 41 to provide a tack free portion 13 for a user to grasp when removing the fastening tape tab portion 41 from the release tab portion 2 of the backsheet 11.

Preferably, the fastening tape tab is further provided with a release layer, allowing the fastening tape tab, or a closure tape laminate, including the fastening tape tab and a release tab provided with a pressure-sensitive adhesive layer, to be formed into a roll of closure tape laminate. An alternative closure laminate is formed of the release tab and the fastening tape tab with no adhesive layer 8 on the release tab and preferably no release layer on surface 5 of the fastening tape tab. In this embodiment, the closure laminate is cut into closure tab laminates and applied to an outer edge region 3 with a hot melt adhesive or the like. In any event, the closure tab laminate or the closure tape tab laminate of the two tabs (1 and 2) are attached to one face of the outer edge region 3 with adhesive layer 8 or some other suitable attachment means.

The fastening tape tab portion 41 is attached to a second face of the outer edge region 3 with a pressure-sensitive adhesive hinge tape 16. The hinge tape 16 can be provided with a more aggressive pressure-sensitive adhesive, such as that used for pressure-sensitive layer 8. Other suitable adhesives are those such as described for adhesive layer 6 with a higher level of polymer (e.g. 50 to 95 percent) and/or with a CMTg of from 250° to 270° Kelvin.

The hinge tape 16 backing 18 can be any suitable substrate, such as those used for the fastening tape tab backing 44. Preferably, the hinge tape backing 18 is a thin, strong film such as an oriented film, such as biaxially oriented polypropylene of a thickness ranging from 10 to 80 microns. The fastening tape tab backing is preferably a softer film or film laminate of a cast unoriented thermoplastic polymer, such as disclosed in U.S. Pat. No. 4,769,283 (Sipinen et al.). The hinge tape backing can be stiffer than the fastening tape tab backing as it does not extend out beyond the outer edge region 3 without being attached to the fastening tape tab portion. Therefore, the hinge tape backing is much less likely, than the fastening tape tab portion backing, to come into direct contact with the user or wearer and cause irritation. The hinge tape is preferably 15 to 90 percent the size of the fastening tape tab portion with at least 1.0 cm attached to the second face of the outer edge region and the, which preferably is said backsheet layer.

Figure 4:
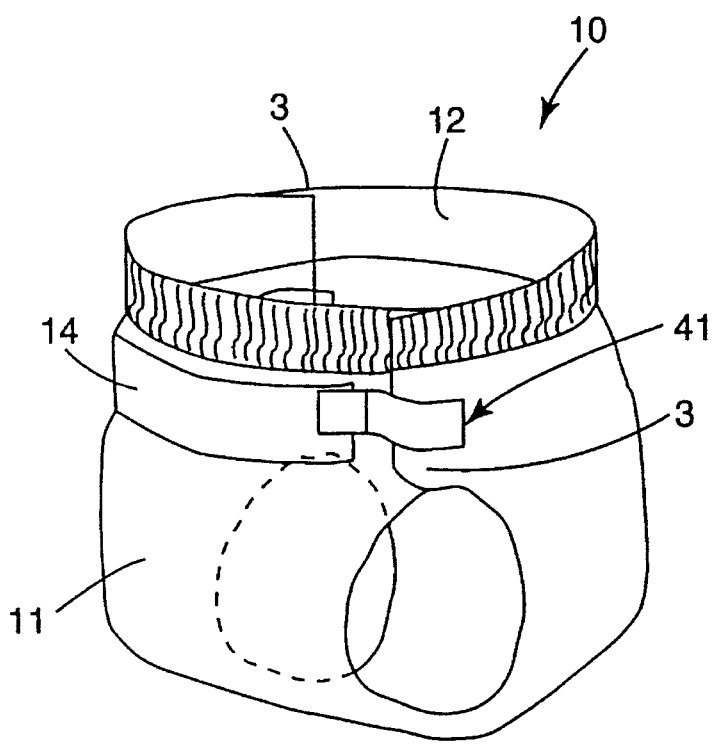
FIG. 4 is a perspective view of the invention closure tape tab system on a diaper.

FIG. 4 is a depiction of the invention diaper closure tape tab system as it would appear when in use on a diaper 10. The diaper 10 is of a conventional design with the fastening tape tab portion 1 shown releasably attached to a frontal region 14 and permanently attached to ears or edge regions 3 on the diaper 10. The frontal region 14 can be provided with a reinforcement film, or the like to increase strength in this area, if required, as is known in the art.

Figure 5:
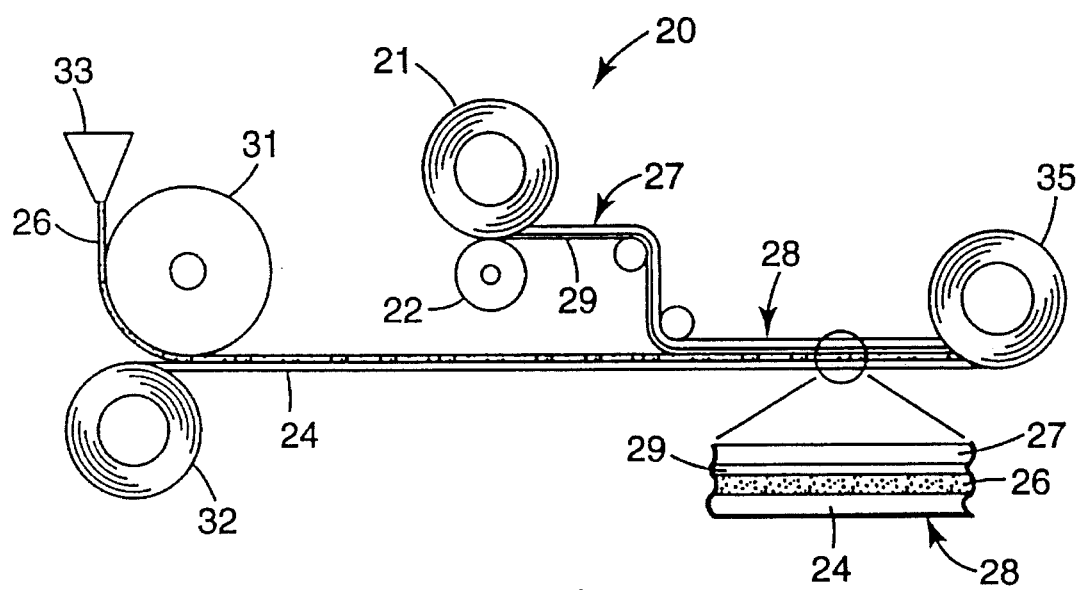
FIG. 5 is a schematic view of a method of manufacturing a closure laminate used in the invention closure tape tab system.

FIG. 5 illustrates schematically a method of manufacturing a closure laminate 28 of a release tab 27 and a fastening tape tab 25 used in the invention closure tape tab system. The backing 24 for the fastening tape tab 25 is provided on a feed roll 32 which unwinds into a chilled nip roll 31. Pressure-sensitive adhesive is provided by an extruder or other suitable feed means 33 into the nip or on the chill roll 31 forming the pressure-sensitive adhesive layer 26. The formed fastening tab tape 25 is then laminated with a release tab 27 provided from a roll 20 of release tab backing 21, which can be previously coated with a release coating 29 or coated with a suitable release material on line to form the release tab 27. The release coated 29 face of the release tab backing 21 is laminated to the pressure-sensitive adhesive layer 26 on the fastening tape tab backing 24. The closure laminate 28 can then be collected in roll form 35. An adhesive layer could also be coated on release tab backing 21 and a release layer coated on backing 24 to form a closure tape laminate which could also be collected in a roll as a tape laminate, or used directly on a diaper line as a closure tape laminate, and cut into a closure tape tab laminate. A roll of the closure laminate 35 would be unwound, then cut into closure tab laminates and coated with adhesive (either before or after cutting the laminate into tab laminates), or otherwise attached to a diaper on the diaper line.

Figure 6:
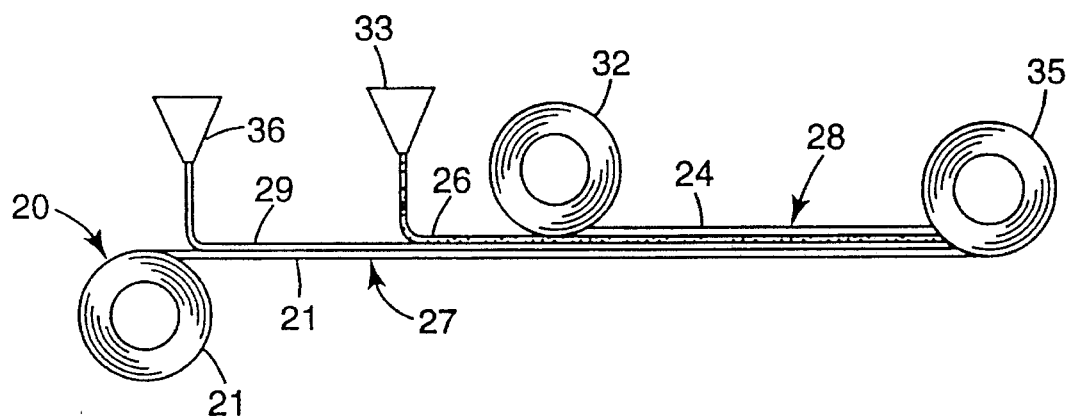
FIG. 6 is a schematic view of a second method of manufacturing a closure laminate used in the invention closure tape tab system with a side view of a second embodiment closure tab laminate.

FIG. 6 schematically illustrates an alternative method of forming a closure laminate which can be cut into closure tab laminates, such as shown in FIG. 2. In this embodiment, the release tab backing 21 is supplied from supply roll 20 and coated with a release material 36. Subsequently, the release tab 27 is coated with a pressure-sensitive adhesive with a coater 33 onto the previously applied release material 36, forming pressure-sensitive adhesive layer 26. The release material 36 forms release coating 29, having had time to sufficiently cure, which prevents intermingling of the release coating and the pressure-sensitive adhesive. The fastening tape tab backing 24, from supply roll 32, is then laminated onto the adhesive layer 26 and the closure laminate collected as roll 35. When the closure laminate 28 is unwound and cut into closure tab laminates and the fastening tape tab portion is subsequently removed from the release tab, the adhesive 26 will remain bonded to the fastening tape tab backing 24 releasing from release tab backing 21.

Figure 7:
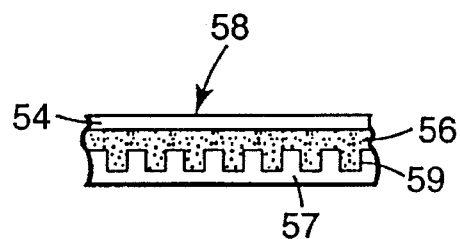
FIG. 7 is a side view of a portion of a structured release tape laminate useful in the invention closure tape tab system.

In FIG. 7 the release tab backing 57 is shown as having a structured surface. The adhesive when applied to backing 57 in a liquid or flowable form as per the FIG. 6 method will conform to this structured surface forming a mirror image structured adhesive layer 56. The method of FIG. 5 could likewise be used to form a structured adhesive surface by cold flow of the adhesive while in roll 35, or preferably by passing the closure laminate 58 through a suitable nip under pressure, and optionally heat, while the adhesive is still somewhat flowable. Generally, the average peak to base height of the structure is from 15 to 500 micron, preferably 25 to 250 microns.

In FIG. 7, the adhesive structure of the fastening tape tab adhesive layer 56 can be maintained due to the exact mating of the adhesive layer 56 with the structures on the release tab backing 57, both while the closure laminate is in roll form and while the closure laminate is on the diaper as a tab. As such the fastening tape tab adhesive 56 can maintain the fidelity of it's structure up a fastening tape tab portion is removed from a release tab portion and placed on the diaper. The advantages of a structured adhesive on the fastening tape tab portion include control of adhesive properties such as tack, peel noise level and adhesive/substrate surface matching. These structured adhesives are particularly useful in providing tape tabs with low peel noise levels when removed from a substrate, as is disclosed in PCT application Ser. No. 94/10837 (Boyer et al.). The provision of a structured adhesive, by using a structured release tab, in a conventional closure system, as shown in FIG. 1, must be done by use of a pressure nip on the diaper line. This is a less effective method as the adhesive generally does not have sufficient time to conform to the release tape tab portion structure. The FIG. 6 embodiment is overall preferred for importing structure onto a fastening tape tab adhesive layer.

I claim:

1. A disposable garment pressure-sensitive adhesive closure tape tab system comprising a closure tab laminate, comprised of a fastening tape tab portion having a substrate with a first and second face, and a release tab portion having a substrate with a first and second face, and a hinge tape having a substrate with a first face and a second face, the release tab portion substrate first face having a release layer with no release layer on said second face, said fastening tape tab portion first face having an adhesive layer, said two tab portions first faces are releasably attached to each other, such that the fastening tape tab portion adhesive layer does not form a permanent adhesive bond to said release tab with said fastening tape tab portion first face in face-to-face contact with said release tape tab portion first face, the release tab portion second face is attached to a first face of a disposable garment adjacent an edge thereof, said hinge tape first face coated with a pressure-sensitive adhesive layer, a first end of the hinge tape first face permanently adhesively attached to said fastening tape tab portion second face and a second end of said hinge tape first face permanently adhesively attached to said disposable garment second face adjacent said edge and opposite said release tab portion thereby permanently attaching the fastening tape tab to the disposable garment wherein the fastening tape tab second face has no adhesive layer other than that provided by the adhesive layer on the first end of the hinge tape second face.

2. The closure tape tab system of claim 1 wherein said fastening tape tab portion second face comprises a release layer and said release tab portion second face has an adhesive layer forming a release tape tab.

3. The tape closure system of claim 2 wherein said release tape tab portion and said fastening tape tab portion are coextensive, with the entire fastening tape tab releasable from the release tape tab portion.

4. The tape closure system of claim 3 wherein said fastening tape tab portion adhesive layer is less aggressive than said hinge tape adhesive layer.

5. The tape closure system of claim 1 wherein said release tab portion first face has a structured surface and the fastening tape tab portion first face pressure-sensitive adhesive is in mating contact with said structured surface forming a structured pressure-sensitive adhesive layer.

6. The tape closure system of claim 5 wherein said release tab first face structures are at least 25 microns high.

7. The tape closure system of claim 1 wherein said hinge tape backing is an oriented thermoplastic polymer film.

8. The tape closure system of claim 7 wherein said hinge tape backing is 10 to 80 microns thick.

9. The tape closure system of claim 7 wherein said hinge tape adhesive is more aggressive than said fastening tape tab first face adhesive layer and is 15 to 90 percent of the size of the fastening tape tab with at least 1.0 cm of said hinge tape attached to said disposable garment second face.

10. The tape closure system of claim 9 wherein said disposable garment comprises a disposable diaper with said disposable garment first face being a water permeable topsheet layer and said disposable garment second face being a water impermeable backsheet layer.

\* \* \* \* \*